United States Patent
Wynn et al.

(10) Patent No.: US 10,301,256 B2
(45) Date of Patent: *May 28, 2019

(54) SULFONAMIDE AND SULFINAMIDE PRODRUGS OF FUMARATES AND THEIR USE IN TREATING VARIOUS DISEASES

(71) Applicant: Alkermes Pharma Ireland Limited, Dublin (IE)

(72) Inventors: Thomas Andrew Wynn, Lexington, MA (US); Christopher P. Hencken, Boston, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/363,610

(22) Filed: Nov. 29, 2016

(65) Prior Publication Data

US 2017/0129851 A1    May 11, 2017

Related U.S. Application Data

(63) Continuation of application No. 14/630,248, filed on Feb. 24, 2015, now Pat. No. 9,604,922.

(60) Provisional application No. 61/943,699, filed on Feb. 24, 2014.

(51) Int. Cl.

| | | |
|---|---|---|
| *C07D 275/06* | (2006.01) | |
| *C07D 275/02* | (2006.01) | |
| *C07C 311/06* | (2006.01) | |
| *C07C 311/29* | (2006.01) | |
| *C07C 311/48* | (2006.01) | |
| *C07C 313/06* | (2006.01) | |
| *C07C 311/04* | (2006.01) | |
| *C07C 311/09* | (2006.01) | |
| *C07C 311/17* | (2006.01) | |

(52) U.S. Cl.
CPC .......... *C07C 311/06* (2013.01); *C07C 311/04* (2013.01); *C07C 311/09* (2013.01); *C07C 311/17* (2013.01); *C07C 311/29* (2013.01); *C07C 311/48* (2013.01); *C07C 313/06* (2013.01); *C07D 275/02* (2013.01); *C07D 275/06* (2013.01)

(58) Field of Classification Search
CPC ... C07D 275/06; C07D 275/02; C07C 311/06; C07C 311/29; C07C 311/48; C07C 313/06

See application file for complete search history.

(56) References Cited

U.S. PATENT DOCUMENTS 3,549,770 A  * 12/1970  Jacob ................ A61K 8/46
                                                514/708
9,604,922 B2 *  3/2017  Wynn ................ C07C 311/04

FOREIGN PATENT DOCUMENTS

EP        0243605  A2     2/1987

OTHER PUBLICATIONS

Chemical Abstracts Registry No. 1110882-23-9, indexed in the Registry file on STN CAS Online Feb. 24, 2009.*
Aurora Fine Chemicals website snapshot on The Wayback Machine, http://web.archive.org/web/20120315212820/http://www.aurorafinechemicals.com/free-compounds.html, Mar. 15, 2012.*
Product Information from Aurora Fine Chemicals on the compound of Catalog No. K05.754.647, accessed Sep. 7, 2016 and Aurora Fine Chemicals News on Compounds for free, Feb. 2012.*
Handbook of Pharmaceutical Excipients, Fourth Edition, Raymond C. Rowe, Ed., Pharmaceutical Press and American Pharmaceutical Association, 2003, pp. 219-221.*

* cited by examiner

*Primary Examiner* — Laura L Stockton
(74) *Attorney, Agent, or Firm* — Elmore Patent Law Group, P.C.; Carolyn Elmore; Joseph Zucchero

(57) ABSTRACT

The present invention provides compounds and pharmaceutical compositions for treating neurological diseases such as multiple sclerosis.

15 Claims, 5 Drawing Sheets

SULFONAMIDE AND SULFINAMIDE PRODRUGS OF FUMARATES AND THEIR USE IN TREATING VARIOUS DISEASES

RELATED APPLICATIONS

This application is a continuation application of U.S. application Ser. No. 14/630,248, filed Feb. 24, 2015, which claims the benefit of U.S. Provisional Application No. 61/943,699, filed on Feb. 24, 2014. The entire teachings of the above applications are incorporated herein by reference.

FIELD OF THE INVENTION

Provided herein are various prodrugs of monomethyl fumarate. In particular, provided herein are sulfonamide and sulfinamide derivatives of monomethyl fumarate. The invention also relates to methods of treating various diseases.

BACKGROUND OF THE INVENTION

Fumaric acid esters (FAEs) are approved in Germany for the treatment of psoriasis, are being evaluated in the United States for the treatment of psoriasis and multiple sclerosis, and have been proposed for use in treating a wide range of immunological, autoimmune, and inflammatory diseases and conditions.

FUMADERM®, an enteric coated tablet containing a salt mixture of monoethyl fumarate and dimethyl fumarate (DMF), which is rapidly hydrolyzed to monomethyl fumarate, regarded as the main bioactive metabolite, was approved in Germany in 1994 for the treatment of psoriasis. FUMADERM® is dosed TID (ter in die, three times a day) with 1-2 grams/day administered for the treatment of psoriasis. FUMADERM® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, *Clin Expt'l Dermatology* 2007, 32, 246-49; and Hoefnagel et al., *Br J Dermatology* 2003, 149, 363-369). Side effects of current FAE therapy include gastrointestinal upset including nausea, vomiting, diarrhea and/or transient flushing of the skin.

Multiple sclerosis (MS) is an autoimmune disease with the autoimmune activity directed against central nervous system (CNS) antigens. The disease is characterized by inflammation in parts of the CNS, leading to the loss of the myelin sheathing around neuronal axons (gradual demyelination), axonal loss, and the eventual death of neurons, oligodendrocytes and glial cells. Dimethyl fumarate (DMF) is the active component of the experimental therapeutic, BG-12, studied for the treatment of relapsing-remitting MS (RRMS). In a Phase IIb RRMS study, BG-12 significantly reduced gadolinium-enhancing brain lesions. In preclinical studies, DMF administration has been shown to inhibit CNS inflammation in murine and rat experimental autoimmune encephalomyelitis (EAE). It has also been found that DMF can inhibit astrogliosis and microglial activations associated with EAE. See, e.g., US Published Application No. 2012/0165404.

TECFIDERA®, a hard gelatin delayed-release capsule containing DMF, which is rapidly hydrolyzed to monomethyl fumarate, was approved in the United States in 2013 for the treatment of relapsing multiple sclerosis. TECFIDERA® is dosed BID (bis in die, two times a day) with a total daily dose of about 240 mg to 480 mg. Peak levels are achieved 2-2.5 hours after oral administration.

However, dimethyl fumarate is also associated with significant drawbacks. For example, dimethyl fumarate is known to cause side effects upon oral administration, such as flushing and gastrointestinal events including nausea, diarrhea, and/or upper abdominal pain in subjects. See, e.g., Gold et al., *N. Engl. J. Med.*, 2012, 367(12), 1098-1107. Dimethyl fumarate is dosed BID or TID with a total daily dose of about 480 mg to about 1 gram or more. Further, in the use of a drug for long-term therapy, it is desirable that the drug be formulated so that it is suitable for once- or twice-daily administration to aid patient compliance. A dosing frequency of once-daily or less is even more desirable.

Another problem with long-term therapy is the requirement of determining an optimum dose which can be tolerated by the patient. If such a dose is not determined, this can lead to a diminution in the effectiveness of the drug being administered.

There remains a need for compounds and methods for the treatment of neurological disease.

SUMMARY OF THE INVENTION

The methods and compositions described herein comprise one or more prodrugs (e.g., sulfonamide-containing or sulfinamide-containing prodrugs) of monomethyl fumarate (MMF). The compounds of the invention can be converted in vivo, upon oral administration, to monomethyl fumarate. Upon conversion, the active moiety (i.e., monomethyl fumarate) is effective in treating subjects suffering from a neurological disease.

The present invention provides, in part, a compound of Formula (I), or a pharmaceutically acceptable salt thereof:

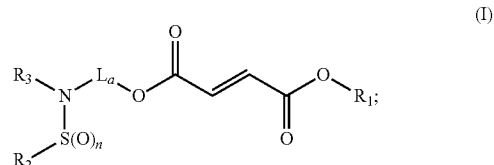

(I)

wherein:

$R_1$ is $C_1$-$C_6$ alkyl;

$L_a$ is $C_1$-$C_6$ alkyl, $C_3$-$C_{10}$ carbocycle, $C_6$-$C_{10}$ aryl, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, carbocycle, aryl, heterocycle, or heteroaryl groups are optionally, independently substituted one or more times with halogen;

$R_2$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_3$ is H, $C_1$-$C_{10}$ alkyl, $C_2$-$C_6$ alkenyl, $C_2$-$C_6$ alkynyl, $SO_2R_4$, or $S(O)R_4$, wherein the alkyl, alkenyl, or alkynyl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_4$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2.

Also provided herein are pharmaceutical compositions comprising one or more compounds of any of the formulae described herein and one or more pharmaceutically acceptable carriers.

In one aspect, provided herein are methods of treating a neurological disease by administering to a subject in need thereof a therapeutically effective amount of a compound of any of the formulae described herein, or a pharmaceutically acceptable salt thereof, such that the neurological disease is treated.

In another aspect, provided herein are methods of treating multiple sclerosis by administering to a subject in need thereof a therapeutically effective amount of a compound of any of the formulae described herein, or a pharmaceutically acceptable salt thereof, such that the multiple sclerosis is treated.

In another aspect, provided herein are methods of treating relapsing-remitting multiple sclerosis (RRMS) by administering to a subject in need thereof a therapeutically effective amount of a compound of any of the formulae described herein, or a pharmaceutically acceptable salt thereof, such that the relapsing-remitting multiple sclerosis is treated.

In another aspect, provided herein are methods of treating secondary progressive multiple sclerosis (SPMS) by administering to a subject in need thereof a therapeutically effective amount of a compound of any of the formulae described herein, or a pharmaceutically acceptable salt thereof, such that the secondary progressive multiple sclerosis is treated.

In another aspect, provided herein are methods of treating primary progressive multiple sclerosis (PPMS) by administering to a subject in need thereof a therapeutically effective amount of a compound of any of the formulae described herein, or a pharmaceutically acceptable salt thereof, such that the primary progressive multiple sclerosis is treated.

In another aspect, provided herein are methods of treating progressive relapsing multiple sclerosis (PRMS) by administering to a subject in need thereof a therapeutically effective amount of a compound of any of the formulae described herein, or a pharmaceutically acceptable salt thereof, such that the progressive relapsing multiple sclerosis is treated.

In another aspect, provided herein are methods of treating Alzheimer's disease by administering to a subject in need thereof a therapeutically effective amount of a compound of any of the formulae described herein, or a pharmaceutically acceptable salt thereof, such that the Alzheimer's disease is treated.

In another aspect, provided herein are methods of treating cerebral palsy by administering to a subject in need thereof a therapeutically effective amount of a compound of any of the formulae described herein, or a pharmaceutically acceptable salt thereof, such that the cerebral palsy is treated.

In another aspect, provided herein are methods of treating psoriasis by administering to a subject in need thereof a therapeutically effective amount of a compound of any of the formulae described herein, or a pharmaceutically acceptable salt thereof, such that the psoriasis is treated.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
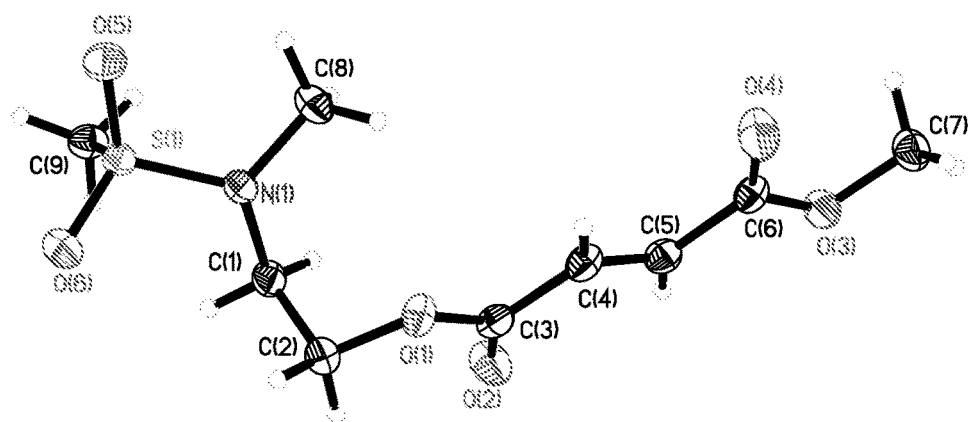
FIG. 1 depicts the single crystal X-ray structure of compound 1.

Provided herein are compounds and methods of treating a neurological disease by administering a compound of Formula (I), synthetic methods for making a compound of Formula (I), and pharmaceutical compositions containing a compound of Formula (I).

Also provided herein are compounds and methods for the treatment of psoriasis by administering to a subject in need thereof, a therapeutically effective amount of a compound of Formula (I), or a pharmaceutically acceptable salt thereof.

Also provided are methods for the treatment of a neurological disease by administering to a subject in need thereof, a therapeutically effective amount of a compound of Formula (I), or a pharmaceutically acceptable salt thereof. The neurological disease can be multiple sclerosis.

There are four major clinical types of MS: 1) relapsing-remitting MS (RRMS), characterized by clearly defined relapses with full recovery or with sequelae and residual deficit upon recovery; periods between disease relapses characterized by a lack of disease progression; 2) secondary progressive MS (SPMS), characterized by initial relapsing remitting course followed by progression with or without occasional relapses, minor remissions, and plateaus; 3) primary progressive MS (PPMS), characterized by disease progression from onset with occasional plateaus and temporary minor improvements allowed; and 4) progressive relapsing MS (PRMS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS (RRMS) presents in the form of recurrent attacks of focal or multifocal neurologic dysfunction. Attacks may occur, remit, and recur, seemingly randomly over many years. Remission is often incomplete and as one attack follows another, a stepwise downward progression ensues with increasing permanent neurological deficit. The usual course of RRMS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits, as defined above and either from onset or after a period of episodes, but this designation does not preclude the further occurrence of new relapses.

In another aspect, provided herein is the use of a compound of Formula (I), or a pharmaceutically acceptable salt thereof, for the preparation of a medicament useful for the treatment of a neurological disease.

According to the present invention, a neurological disease is a disorder of the brain, spinal cord or nerves in a subject. In one embodiment, the neurological disease is characterized by demyelination, or degeneration of the myelin sheath, of the central nervous system. The myelin sheath facilitates the transmission of nerve impulses through a nerve fiber or axon. In another embodiment, the neurological disease is selected from the group consisting of multiple sclerosis, Alzheimer's disease, cerebral palsy, spinal cord injury, Amyotrophic lateral sclerosis (ALS), stroke, Huntington's disease, Parkinson's disease, optic neuritis, Devic disease, transverse myelitis, acute disseminated encephalomyelitis, adrenoleukodystrophy and adrenomyeloneuropathy, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyelitis (ADEM), and other hereditary disorders, such as leukodystrophies, Leber's optic atrophy, and Charcot-Marie-Tooth disease. In some embodiments, the neurological disorder is an auto-immune disease. In one embodiment, the neurological disease is multiple sclerosis. In another embodiment, the neurological disease is stroke. In another embodiment, the neurological disease is Alzheimer's disease. In another embodiment, the neurological disease is cerebral palsy. In another embodiment, the neurological disease is spinal cord injury. In another embodiment, the neurological disease is ALS. In another embodiment, the neurological disease is Huntington's disease. See, e.g., U.S. Pat. No. 8,007,826, WO2005/099701 and WO2004/082684, which are incorporated by reference in their entireties.

Also provided herein are methods for the treatment of a disease or a symptom of a disease described herein by administering to a subject in need thereof a therapeutically effective amount of a compound of Formula (I), or a pharmaceutically acceptable salt thereof.

In one aspect, provided herein is the use of a compound of Formula (I), or a pharmaceutically acceptable salt thereof for the treatment of a disease or a symptom of a disease described herein.

In several aspects, provided herein is a compound of the invention (i.e., a compound of Formula (I), or a pharmaceutically acceptable salt thereof), and a method for the treatment of a neurological disease by administering to a subject in need thereof, a therapeutically effective amount of a compound of the invention. In another aspect, provided herein is a compound of the invention (i.e., a compound of Formula (I), or a pharmaceutically acceptable salt thereof) for use in treating a neurological disease.

In one embodiment, the compound of the invention is the compound of Formula (I). In another embodiment, the compound of the invention is the compound of Formula (I), or a pharmaceutically acceptable salt thereof. In still another embodiment, the compound of the invention is a pharmaceutically acceptable salt of the compound of Formula (I).

The compound of Formula (I) has the structure:

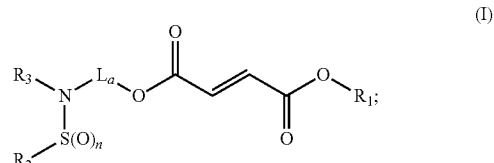

wherein $R_1$ is $C_1$-$C_6$ alkyl;

$L_a$ is $C_1$-$C_6$ alkyl, $C_3$-$C_{10}$ carbocycle, $C_6$-$C_{10}$ aryl, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, carbocycle, aryl, heterocycle, or heteroaryl groups are optionally, independently substituted one or more times with halogen;

$R_2$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_3$ is H, $C_1$-$C_{10}$ alkyl, $C_2$-$C_6$ alkenyl, $C_2$-$C_6$ alkynyl, $SO_2R_4$, or $S(O)R_4$, wherein the alkyl, alkenyl, or alkynyl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_4$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2.

In one embodiment of Formula (I), $L_a$ is $C_1$-$C_6$ alkyl, wherein the alkyl is substituted one or more times with halogen, and wherein the halogen is fluorine. In another embodiment, $L_a$ is $C_1$-$C_6$ alkyl, wherein the alkyl is substituted one or two times with halogen, and wherein the halogen is fluorine.

In another embodiment of Formula (I), or a pharmaceutically acceptable salt thereof, $R_1$ is $C_1$-$C_6$ alkyl;

$L_a$ is $C_1$-$C_6$ alkyl, $C_3$-$C_{10}$ carbocycle, $C_6$-$C_{10}$ aryl, heterocycle comprising one or two 5- or 6-membered rings and 1-4 heteroatoms selected from N, O and S, or heteroaryl comprising one or two 5- or 6-membered rings and 1-4 heteroatoms selected from N, O and S;

$R_2$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_3$ is H, $C_1$-$C_{10}$ alkyl, $C_2$-$C_6$ alkenyl, $C_2$-$C_6$ alkynyl, $SO_2R_4$, or S(O)$R_4$;

$R_4$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2.

In one embodiment of the compound of Formula (I), $R_1$ is methyl.

In another embodiment of the compound of Formula (I), $R_2$ is $C_1$-$C_{10}$ alkyl, $C_1$-$C_{10}$ alkyl substituted one or more times with halogen, or phenyl optionally substituted one or more times with $C_1$-$C_6$ alkyl, OH, O($C_1$-$C_6$ alkyl), or halogen.

In yet another embodiment of the compound of Formula (I), $R_3$ is H or $C_1$-$C_{10}$ alkyl.

In still another embodiment of the compound of Formula (I), $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo.

In another embodiment of the compound of Formula (I), $L_a$ is $C_1$-$C_6$ alkyl. In a particular embodiment, $L_a$ is $(CH_2)_2$.

In yet another embodiment of the compound of Formula (I), $R_1$ is $C_1$-$C_6$ alkyl; $L_a$ is a $C_1$-$C_6$ alkyl; $R_2$ is $C_1$-$C_{10}$ alkyl optionally substituted by halogen, or $C_6$-$C_{10}$ aryl optionally substituted by $C_1$-$C_{10}$ alkyl; $R_3$ is H, $C_1$-$C_{10}$ alkyl, $SO_2R_4$, or S(O)$R_4$; $R_4$ is $C_1$-$C_{10}$ alkyl optionally substituted by halogen, or $C_6$-$C_{10}$ aryl optionally substituted by $C_1$-$C_{10}$ alkyl; or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2.

In one embodiment, the compound of the invention is the compound of Formula (Ia). In another embodiment, the compound of the invention is the compound of Formula (Ia), or a pharmaceutically acceptable salt thereof. In still another embodiment, the compound of the invention is a pharmaceutically acceptable salt of the compound of Formula (Ia).

The compound of Formula (Ia) has the structure:

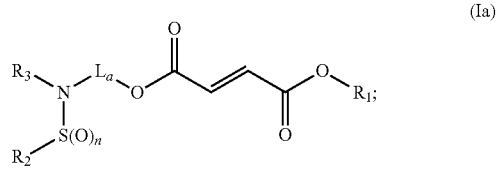

(Ia)

wherein:

$R_1$ is $C_1$-$C_6$ alkyl;

$L_a$ is $C_1$-$C_6$ alkyl, $C_3$-$C_{10}$ carbocycle, $C_6$-$C_{10}$ aryl, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, carbocycle, aryl, heterocycle, or heteroaryl groups are optionally, independently substituted one or more times with $C_1$-$C_6$ alkyl or halogen;

$R_2$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_3$ is H, $C_1$-$C_{10}$ alkyl, $C_2$-$C_6$ alkenyl, $C_2$-$C_6$ alkynyl, $SO_2R_4$, or S(O)$R_4$, wherein the alkyl, alkenyl, or alkynyl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

$R_4$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, O($C_1$-$C_6$ alkyl), oxo, halogen, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;

or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2.

In one embodiment of the compound of Formula (Ia), $L_a$ is $C_1$-$C_6$ alkyl optionally substituted one or more times with $C_1$-$C_6$ alkyl.

Multiple embodiments of the invention are represented by the following examples:

For example, the neurological disease is multiple sclerosis.

For example, the neurological disease is relapsing-remitting multiple sclerosis (RRMS).

For example, the neurological disease is secondary progressive multiple sclerosis.

For example, the neurological disease is primary progressive multiple sclerosis.

For example, the neurological disease is progressive relapsing multiple sclerosis.

For example, the compound of Formula (I) is a compound listed in Table 1 herein.

For example, in the compound of Formula (I), $R_1$ is methyl.

For example, in the compound of Formula (I), $R_1$ is ethyl.

For example, in the compound of Formula (I), $L_a$ is $C_1$-$C_6$ alkyl linker.

For example, in the compound of Formula (I), $L_a$ is $C_1$-$C_3$ alkyl linker.

For example, in the compound of Formula (I), $L_a$ is $C_2$ alkyl linker.

For example, in the compound of Formula (I), $L_a$ is unsubstituted $C_2$ alkyl linker.

For example, in the compound of Formula (I), $L_a$ is methyl substituted $C_2$ alkyl linker.

For example, in the compound of Formula (I), $L_a$ is di-methyl substituted $C_2$ alkyl linker.

For example, in the compound of Formula (I), $L_a$ is methyl or di-methyl substituted $C_2$ alkyl linker.

For example, in the compound of Formula (I), $R_2$ is $C_1$-$C_{10}$ alkyl.

For example, in the compound of Formula (I), $R_2$ is $C_1$-$C_6$ alkyl.

For example, in the compound of Formula (I), $R_2$ is unsubstituted $C_1$-$C_6$ alkyl.

For example, in the compound of Formula (I), $R_2$ is $C_1$-$C_3$ alkyl.

For example, in the compound of Formula (I), $R_2$ is unsubstituted $C_1$-$C_3$ alkyl.

For example, in the compound of Formula (I), $R_2$ is $C_1$-$C_2$ alkyl.

For example, in the compound of Formula (I), $R_2$ is unsubstituted $C_1$-$C_2$ alkyl.

For example, in the compound of Formula (I), $R_3$ is H.

For example, in the compound of Formula (I), $R_3$ is $C_1$-$C_6$ alkyl.

For example, in the compound of Formula (I), $R_3$ is unsubstituted $C_1$-$C_6$ alkyl.

For example, in the compound of Formula (I), $R_2$ is $C_6$-$C_{10}$ aryl.

For example, in the compound of Formula (I), $R_2$ is unsubstituted $C_6$-$C_{10}$ aryl.

For example, in the compound of Formula (I), $R_2$ is phenyl.

For example, in the compound of Formula (I), $R_2$ is unsubstituted phenyl.

For example, in the compound of Formula (I), $R_2$ is benzyl.

For example, in the compound of Formula (I), $R_2$ is unsubstituted benzyl.

For example, the compound is a compound listed in Table 1 herein, or a pharmaceutically acceptable salt thereof.

Representative compounds of the present invention include compounds listed in Table 1.

TABLE 1

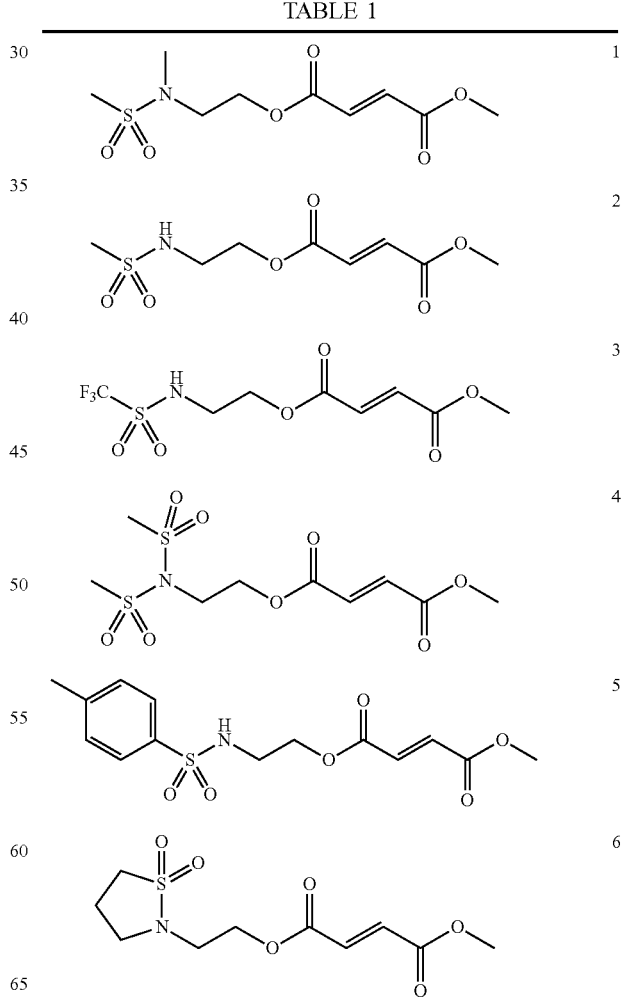

TABLE 1-continued

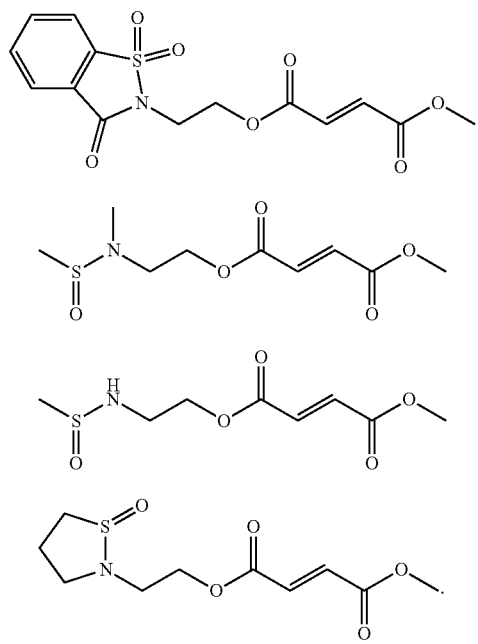

Also provided herein are pharmaceutical compositions comprising a therapeutically effective amount of a compound of Formula (I), or a pharmaceutically acceptable salt thereof, and a pharmaceutically acceptable carrier or excipient. In one embodiment, the therapeutically effective amount is sufficient for the treatment of a neurological disorder. In a particular embodiment, the neurological disorder is secondary progressive multiple sclerosis. In a particular embodiment, the neurological disorder is primary progressive multiple sclerosis. In a particular embodiment, the neurological disorder is progressive relapsing multiple sclerosis. In another particular embodiment, the neurological disorder is relapsing-remitting multiple sclerosis. In another particular embodiment, the neurological disorder is Alzheimer's disease.

In one embodiment, the pharmaceutical composition is a controlled release composition comprising a compound of Formula (I), or a pharmaceutically acceptable salt thereof, and one or more pharmaceutically acceptable carriers, wherein the controlled release composition provides a therapeutically effective amount of monomethyl fumarate to a subject. In another embodiment, the pharmaceutical composition is a controlled release composition comprising a compound of Formula (I), or a pharmaceutically acceptable salt thereof, and one or more pharmaceutically acceptable carriers, wherein the controlled release composition provides a therapeutically effective amount of monomethyl fumarate to a subject for at least about 8 hours to at least about 24 hours. In another embodiment, the pharmaceutical composition is a controlled release composition comprising a compound of Formula (I), or a pharmaceutically acceptable salt thereof, and one or more pharmaceutically acceptable carriers, wherein the controlled release composition provides a therapeutically effective amount of monomethyl fumarate to a subject for at least about 8 hours, at least about 10 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours or longer. For example, at least about 18 hours. For example, at least about 12 hours. For example, greater than 12 hours.

For example, at least about 16 hours. For example, at least about 20 hours. For example, at least about 24 hours.

In another embodiment, a compound of Formula (I), or a pharmaceutically acceptable salt thereof, is efficiently converted to the active species, i.e., monomethyl fumarate, upon oral administration. For example, about 50 mole percent, about 55 mole percent, about 60 mole percent, about 65 mole percent, about 70 mole percent, about 75 mole percent, about 80 mole percent, about 85 mole percent, about 90 mole percent, or greater than 90 mole percent of the total dose of a compound of Formula (I), or a pharmaceutically acceptable salt thereof, administered is converted to monomethyl fumarate upon oral administration. In another embodiment, a compound of Formula (I), or a pharmaceutically acceptable salt thereof, is converted to the active species, i.e., monomethyl fumarate, upon oral administration more efficiently than dimethyl fumarate. In another embodiment, a compound of Formula (I), or a pharmaceutically acceptable salt thereof, is converted to the active species, i.e., monomethyl fumarate, upon oral administration more efficiently than one or more of the compounds described in U.S. Pat. No. 8,148,414. U.S. Pat. No. 8,148,414 is expressly incorporated by reference herein. For example, a compound of Formula (I) is essentially completely converted to the active species, i.e., monomethyl fumarate, upon oral administration.

In another embodiment, any one of compounds 1-10, or a pharmaceutically acceptable salt thereof, is efficiently converted to the active species, i.e., monomethyl fumarate, upon oral administration. For example, about 50 percent, about 55 percent, about 60 percent, about 65 percent, about 70 percent, about 75 percent, about 80 percent, about 85 percent, about 90 percent, or greater than 90 percent of the total dose of any one of compounds 1-10, or a pharmaceutically acceptable salt thereof, administered is converted to monomethyl fumarate upon oral administration. In another embodiment, any one of compounds 1-10, or a pharmaceutically acceptable salt thereof, is converted to the active species, i.e., monomethyl fumarate, upon oral administration more efficiently than dimethyl fumarate. In another embodiment, any one of compounds 1-10, or a pharmaceutically acceptable salt thereof, is converted to the active species, i.e., monomethyl fumarate, upon oral administration more efficiently than one or more of the compounds described in U.S. Pat. No. 8,148,414. For example, any one of compounds 1-10, or a pharmaceutically acceptable salt thereof, is completely converted to the active species, i.e., monomethyl fumarate, upon oral administration.

For a drug to achieve its therapeutic effect, it is necessary to maintain the required level of blood or plasma concentration. Many drugs, including dimethyl fumarate, must be administered multiple times a day to maintain the required concentration. Furthermore, even with multiple administrations of such a drug per day, the blood or plasma concentrations of the active ingredient may still vary with time, i.e., at certain time points between administrations there are higher concentrations of the active ingredient than at other times. Thus, at certain time points of a 24-hour period, a patient may receive therapeutically effective amounts of the active ingredient, while at other time points the concentration of the active ingredient in the blood may fall below therapeutic levels. Additional problems with such drugs include that multiple dosing a day often adversely affects patient compliance with the treatment. Therefore, it is desirable to have a drug dosage form wherein the active ingredient is delivered in such a controlled manner that a constant or substantially constant level of blood or plasma concentration of the active ingredient can be achieved by one or at most two dosing per day. Accordingly, the present invention provides controlled-release formulations as described below. In general, such formulations are known to those skilled in the art or are available using conventional methods.

As used herein, "controlled-release" means a dosage form in which the release of the active agent is controlled or modified over a period of time. Controlled can mean, for example, sustained, delayed or pulsed-release at a particular time. For example, controlled-release can mean that the release of the active ingredient is extended for longer than it would be in an immediate-release dosage form, i.e., at least over several hours.

As used herein, "immediate-release" means a dosage form in which greater than or equal to about 75% of the active ingredient is released within two hours, or, more specifically, within one hour, of administration. Immediate-release or controlled-release may also be characterized by their dissolution profiles.

Formulations may also be characterized by their pharmacokinetic parameters. As used herein, "pharmacokinetic parameters" describe the in vivo characteristics of the active ingredient over time, including for example plasma concentration of the active ingredient. As used herein, "$C_{max}$" means the measured concentration of the active ingredient in the plasma at the point of maximum concentration. "$T_{max}$" refers to the time at which the concentration of the active ingredient in the plasma is the highest. "AUC" is the area under the curve of a graph of the concentration of the active ingredient (typically plasma concentration) vs. time, measured from one time to another.

The controlled-release formulations provided herein provide desirable properties and advantages. For example, the formulations can be administered once daily, which is particularly desirable for the subjects described herein. The formulation can provide many therapeutic benefits that are not achieved with corresponding shorter acting, or immediate-release preparations. For example, the formulation can maintain lower, more steady plasma peak values, for example, $C_{max}$, so as to reduce the incidence and severity of possible side effects.

Sustained-release dosage forms release their active ingredient into the gastro-intestinal tract of a patient over a sustained period of time following administration of the dosage form to the patient. Particular dosage forms include: (a) those in which the active ingredient is embedded in a matrix from which it is released by diffusion or erosion; (b) those in which the active ingredient is present in a core which is coated with a release rate-controlling membrane; (c) those in which the active ingredient is present in a core provided with an outer coating impermeable to the active ingredient, the outer coating having an aperture (which may be drilled) for release of the active ingredient; (d) those in which the active ingredient is released through a semipermeable membrane, allowing the drug to diffuse across the membrane or through liquid filled pores within the membrane; and (e) those in which the active ingredient is present as an ion exchange complex.

It will be apparent to those skilled in the art that some of the above means of achieving sustained-release may be combined, for example a matrix containing the active compound may be formed into a multiparticulate and/or coated with an impermeable coating provided with an aperture.

Pulsed-release formulations release the active compound after a sustained period of time following administration of the dosage form to the patient. The release may then be in the form of immediate- or sustained-release. This delay may be achieved by releasing the drug at particular points in the gastro-intestinal tract or by releasing drug after a predetermined time. Pulsed-release formulations may be in the form of tablets or multiparticulates or a combination of both. Particular dosage forms include: (a) osmotic potential triggered release (see U.S. Pat. No. 3,952,741); (b) compression coated two layer tablets (see U.S. Pat. No. 5,464,633); (c) capsules containing an erodible plug (see U.S. Pat. No. 5,474,784); sigmoidal releasing pellets (referred to in U.S. Pat. No. 5,112,621); and (d) formulations coated with or containing pH-dependent polymers including shellac, phthalate derivatives, polyacrylic acid derivatives and crotonic acid copolymers.

Dual release formulations can combine the active ingredient in immediate release form with additional active ingredient in controlled-release form. For example, a bilayer tablet can be formed with one layer containing immediate-release active ingredient and the other layer containing the active ingredient embedded in a matrix from which it is released by diffusion or erosion. Alternatively, one or more immediate release beads can be combined with one or more beads which are coated with a release rate-controlling membrane in a capsule to give a dual release formulation. Sustained-release formulations in which the active ingredient is present in a core provided with an outer coating impermeable to the active ingredient, the outer coating having an aperture (which may be drilled) for release of the active ingredient, can be coated with drug in immediate release form to give a dual release formulation. Dual release formulations can also combine drug in immediate release form with additional drug in pulsed release form. For example, a capsule containing an erodible plug could liberate drug initially and, after a predetermined period of time, release additional drug in immediate- or sustained-release form.

In some embodiments, the dosage forms to be used can be provided as controlled-release with respect to one or more active ingredients therein using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of additional amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, concentration, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing agent, wetting agent, suspending agent, and a preservative. Additional excipients, such as fillers, sweeteners, flavoring, or coloring agents, may also be included in these formulations.

A formulation of a pharmaceutical composition of the invention suitable for oral administration may be prepared or packaged in the form of a discrete solid dose unit including, but not limited to, a tablet, a hard or soft capsule, a cachet, a troche, or a lozenge, each containing a predetermined amount of the active ingredient. In one embodiment, a formulation of a pharmaceutical composition of the invention suitable for oral administration is coated with an enteric coat.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate and poloxamers. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets, optionally, with laser drilling. Tablets may further comprise a sweetener, a flavoring agent, a coloring agent, a preservative, or some combination of these in order to provide for pharmaceutically elegant and palatable formulations.

Hard capsules comprising the active ingredient may be made using a physiologically degradable composition, such as gelatin or HPMC. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Similarly, "$C_1$-$C_{10}$ alkyl" is intended to include $C_1$, $C_2$, $C_3$, $C_4$, $C_5$, $C_6$, $C_7$, $C_8$, $C_9$ or $C_{10}$ straight chain (linear), saturated, aliphatic hydrocarbon groups and $C_3$, $C_4$, $C_5$, $C_6$, $C_7$, $C_8$, $C_9$ or $C_{10}$ branched, saturated, aliphatic hydrocarbon groups. Examples of alkyl include, but not limited to: methyl, ethyl, n-propyl, i-propyl, n-butyl, s-butyl, t-butyl, n-pentyl, s-pentyl, n-hexyl, n-heptyl, n-octyl, 2-ethyl-hexyl, n-nonyl and n-decyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, "alkyl linker" is intended to include $C_1$, $C_2$, $C_3$, $C_4$, $C_5$, or $C_6$ straight chain (linear) saturated aliphatic hydrocarbon groups and $C_3$, $C_4$, $C_5$, or $C_6$ branched saturated aliphatic hydrocarbon groups. For example, $C_1$-$C_6$ alkyl linker is intended to include $C_1$, $C_2$, $C_3$, $C_4$, $C_5$, and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

"Aryl" includes groups with aromaticity, including "conjugated", or multicyclic, systems with at least one aromatic ring. Examples include phenyl, benzyl, naphthyl, etc. "Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the heteroaryl is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, or indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Stable compound" and "stable structure" are meant to indicate a compound that is sufficiently robust to survive isolation to a useful degree of purity from a reaction mixture, and formulation into an efficacious therapeutic agent.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formulae of the invention (e.g., Formula (I)), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

As used herein, a "subject in need thereof" is a subject having a neurological disease. In one embodiment, a subject in need thereof has multiple sclerosis. A "subject" includes a mammal. The mammal can be any mammal, e.g., a human, primate, bird, mouse, rat, fowl, dog, cat, cow, horse, goat, camel, sheep or a pig. In one embodiment, the mammal is a human.

The present invention provides methods for the synthesis of the compounds of each of the formulae described herein. The present invention also provides detailed methods for the synthesis of various disclosed compounds of the present invention according to the following schemes and as shown in the Examples.

The synthetic processes of the invention can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, polymorph, hydrate, solvate or co-crystal thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry Reactions, Mechanisms, and Structure, 5$^{th}$ edition, John Wiley & Sons: New York, 2001; and Greene, T. W., Wuts, P. G. M., Protective Groups in Organic Synthesis, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with each of the formulae described herein may be prepared according to the following procedures from commercially available starting materials or starting materials which can be prepared using literature procedures. These procedures show the preparation of representative compounds of this invention.

EXPERIMENTAL

General Procedure 1

To a mixture of monomethyl fumarate (MMF) (1.0 equivalent) and HBTU (1.5 equivalents) in dimethylformamide (25 ml per g of MMF) was added Hünigs base (2.0 equivalents). The dark brown solution was stirred for 10 minutes and turned into a brown suspension, before addition of the alcohol (1.0-1.5 equivalents). The reaction was stirred for 18 hours at room temperature. Water was added and the product extracted into ethyl acetate three times. The combined organic layers were washed with water three times, dried with magnesium sulphate, filtered and concentrated in vacuo at 45° C. to give the crude product. The crude product was purified by silica chromatography and in some cases further purified by trituration with diethyl ether to give the clean desired ester product. All alcohols were either commercially available or made following known literature procedures.

As an alternative to HBTU (N,N,N',N'-Tetramethyl-O-(1H-benzotriazol-1-yl)uronium hexafluorophosphate), any one of the following coupling reagents can be used: EDCI/HOBt (N-(3-dimethylaminopropyl)-N'-ethylcarbodiimide hydrochloride/hydroxybenzotriazole hydrate); COMU ((1-cyano-2-ethoxy-2-oxoethylidenaminooxy)dimethylamino-morpholino-carbenium hexafluorophosphate); TBTU (O-(benzotriazol-1-yl)-N,N,N',N'-tetramethyluronium tetrafluoroborate); TATU (O-(7-azabenzotriazole-1-yl)-1,1,3,3-tetramethyluronium tetrafluoroborate); Oxyma (ethyl (hydroxyimino)cyanoacetate); PyBOP ((benzotriazol-1-yloxy)tripyrrolidinophosphonium hexafluorophosphate); HOTT (S-(1-oxido-2-pyridyl)-N,N,N',N'-tetramethylthiuronium hexafluorophosphate); FDPP (pentafluorophenyl diphenylphosphinate); T3P (propylphosphonic anhydride); DMTMM (4-(4,6-dimethoxy-1,3,5-triazin-2-yl)-4-methylmorpholinium tetrafluoroborate); PyOxim ([ethyl cyano(hydroxyimino)acetato-O$^2$]tri-1-pyrrolidinylphosphonium hexafluorophosphate); TSTU (N,N,N',N'-tetramethyl-O—(N-succinimidyl)uronium tetrafluoroborate); TDBTU (O-(3,4-dihydro-4-oxo-1,2,3-benzotriazin-3-yl)-N,N,N',N'-tetramethyluronium tetrafluoroborate); TPTU (O-(2-oxo-1(2H)pyridyl)-N,N,N',N'-tetramethyluronium tetrafluoroborate); TOTU (O-[(ethoxycarbonyl)cyanomethylenamino]-N,N,N',N'-tetramethyluronium tetrafluoroborate); IIDQ (isobutyl 1,2-dihydro-2-isobutoxy-1-quinolinecarboxylate); or PyCIU (chlorodipyrrolidinocarbenium hexafluorophosphate).

As an alternative to Hünig's base (diisopropylethylamine), any one of the following amine bases can be used: triethylamine; tributylamine; triphenylamine; pyridine; lutidine (2,6-dimethylpyridine); collidine (2,4,6-trimethylpyridine); imidazole; DMAP (4-(dimethylamino)pyridine); DABCO (1,4-diazabicyclo[2.2.2]octane); DBU (1,8-diazabicyclo[5.4.0]undec-7-ene); DBN (1,5-diazabicyclo[4.3.0]non-5-ene); or proton Sponge® (N,N,N',N'-tetramethyl-1,8-naphthalenediamine).

General Procedure 2

A mixture of monomethyl fumarate (MMF) (1.3 equivalent), the alkyl mesylate (1 equivalent), and potassium carbonate (1.5 equivalent) in acetonitrile (50 ml per g of MMF) was heated at reflux overnight. The mixture was partitioned between ethyl acetate and saturated aqueous sodium hydrogen carbonate, and the organic phase dried (MgSO$_4$). Filtration and removal of the solvent under reduced pressure gave the crude product which was purified in each case by silica chromatography.

Chemical Analysis/Procedures

The NMR spectra described herein were obtained with a Varian 400 MHz NMR spectrometer using standard techniques known in the art.

Example 1

Compound 1: Methyl (2-(N-methylmethylsulfonamido)ethyl) fumarate

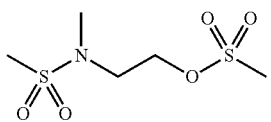

To an ice/methanol cooled mixture of 2-(methylamino)ethanol (10.0 g, 133 mmol) and triethylamine (37.2 mL, 266.4 mmol) in dichloromethane (200 mL) was added methanesulfonyl chloride (20.64 mL, 266.4 mmol) dropwise. The reaction was stirred at room temperature for 2 hours then partitioned between saturated aqueous sodium hydrogen carbonate (300 mL) and dichloromethane (300 mL). The organic phase was washed with brine and dried (MgSO$_4$). Filtration and removal of the solvent under reduced pressure gave 2-(N-methylmethylsulfonamido)ethyl methanesulfonate (22.64 g, 74% yield). $^1$H NMR (300 MHz, CDCl$_3$); 4.37 (2H, t), 3.52 (2H, t), 3.07 (s, 3H), 2.97 (s, 3H), 2.87 (s, 3H).

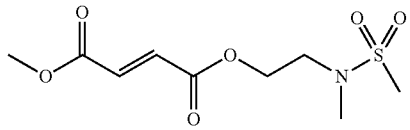

Methyl (2-(N-methylmethylsulfonamido)ethyl) fumarate was synthesised from 2-(N-methylmethylsulfonamido)ethyl methanesulfonate following general procedure 2 (557 mg, 59%). $^1$H NMR (300 MHz, CDCl$_3$); 6.87 (2H, d), 4.37 (2H, t), 3.80 (3H, s), 3.48 (2H, t), 2.95 (3H, s), 2.83 (3H, s). m/z [M+H]$^+$=266.13.

Compound 2: Methyl (2-(methylsulfonamido)ethyl) fumarate

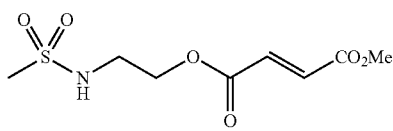 [SMILES: COC(=O)/C=C/C(=O)OCCNS(C)(=O)=O]

Methyl (2-(methylsulfonamido)ethyl) fumarate was synthesised from N-(2-hydroxyethyl)methanesulfonamide following general procedure 1 (319 mg, 39%). $^1$H NMR (300 MHz, CDCl$_3$): δ 6.88 (2H, d), 4.69 (1H, br t), 4.34 (2H, t), 3.82 (3H, s), 3.47 (2H, q), 2.99 (3H, s). m/z [M+H]$^+$=258.11.

Compound 6: 2-(1,1-Dioxidoisothiazolidin-2-yl)ethyl methyl fumarate

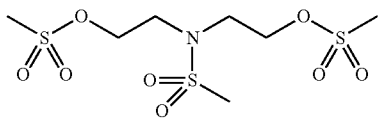

To an ice/methanol cooled mixture of 2,2'-azanediyldiethanol (4.0 g, 38 mmol) and triethylamine (18.5 mL, 122 mmol) in dichloromethane (200 mL) was added methanesulfonyl chloride (9.4 mL, 133 mmol) dropwise. The reaction was stirred at room temperature for 2 hours then partitioned between saturated aqueous sodium hydrogen carbonate (300 mL) and dichloromethane (300 mL). The organic phase was washed with brine and dried (MgSO$_4$). Filtration and removal of the solvent under reduced pressure gave the crude product. This was triturated with diethyl ether giving ((methylsulfonyl)azanediyl(bis(ethane-2,1-diyl) dimethanesulfonate (7.1 g, 55% yield). $^1$H NMR (300 MHz, CDCl$_3$); 4.40 (4H, t), 3.65 (4H, t), 3.08 (s, 6H), 2.98 (3H, s).

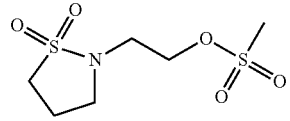

To a suspension of ((methylsulfonyl)azanediyl)bis(ethane-2,1-diyl) dimethanesulfonate (7.1 g, 20.9 mmol) in tetrahydrofuran (100 mL) at 5° C. was added n-BuLi (1.6N in hexanes) (16 mL, 25.6 mmol). After 2 hours the reaction was partitioned between saturated aqueous sodium hydrogen carbonate solution (100 mL) and ethyl acetate (300 mL). The organic phase was dried (MgSO$_4$). Filtration and removal of the solvent under reduced pressure gave the crude material that was purified by silica chromatography (80% ethyl acetate in heptane) giving 2-(1,1-dioxidoisothiazolidin-2-yl)ethyl methanesulfonate (1.90 g, 37% yield). $^1$H NMR (300 MHz, CDCl$_3$); 4.38 (2H, t), 3.43-3.37 (4H, m), 3.16 (2H, t), 3.07 (3H, s), 2.39 (2H, quin).

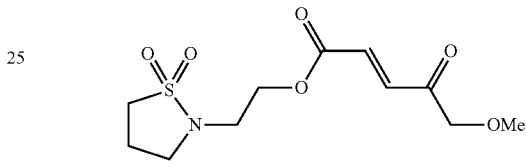

2-(1,1-Dioxidoisothiazolidin-2-yl)ethyl methyl fumarate was synthesised from 2-(1,1-dioxidoisothiazolidin-2-yl) ethyl methanesulfonate following general procedure 2 (367 mg, 31%) $^1$H NMR (300 MHz, CDCl$_3$); 6.88 (2H, d), 4.38 (2H, t), 3.80 (3H, s), 3.36 (4H, t), 3.14 (2H, t), 2.37 (2H, quin). m/z [M+H]$^+$=278.16.

Example 2

Chemical Stability of MMF Prodrugs

Stock solutions of the compounds in acetonitrile or acetonitrile/MeOH were prepared at 0.05M. A 0.010 mL aliquot of the stock was spiked into 1 mL of 50 mM buffer phosphate pH 8 and incubated at 37° C. Typically, aliquots (0.010 mL) were sampled at different time points and immediately injected in the HPLC with UV detection (211 nm). The peak areas corresponding to the compounds were plotted against time and the data were fitted to a first-order mono-exponential decay where the rate constant and the half-life were determined from the slope (Table 2).

TABLE 2

| Compound | pH 8 (t½, min) |
| --- | --- |
| 1 | 187 |
| 2 | 143.5 |
| 6 | 202 |

Example 3

I. Single Crystal X-Ray Data for Compound 1 (FIG. 1):

A colorless needles crystal with dimensions 0.44×0.20× 0.12 mm was mounted on a Nylon loop using very small amount of paratone oil.

Data were collected using a Bruker CCD (charge coupled device) based diffractometer equipped with an Oxford Cryostream low-temperature apparatus operating at 173 K. Data were measured using omega and phi scans of 0.5° per frame for 20 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software which corrects for Lp. Scaling and absorption corrections were applied using SADABS multi-scan technique, supplied by George Sheldrick. The structures are solved by the direct method using the SHELXS-97 program and refined by least squares method on $F^2$, SHELXL-97, which are incorporated in SHELXTL-PC V 6.10.

The structure was solved in the space group P-1 (#2). All non-hydrogen atoms are refined anisotropically. Hydrogens were calculated by geometrical methods and refined as a riding model. The crystal used for the diffraction study showed no decomposition during data collection. All drawings are done at 50% ellipsoids.

Compound 1 produced by the method described in Example 1 was analyzed. FIG. 1 depicts the unit cell. The single crystal x-ray data are included below:

Single Crystal Data:
Empirical formula: C9 H15 N O6 S
Formula weight: 265.28
Temperature: 173(2) K
Wavelength: 1.54178 Å
Space group: P-1
Unit cell dimensions: a=5.41860(10) Å α=103.3520(10)°.
  b=7.49550(10) Å β=90.2790(10)°.
  c=15.4618(3) Å γ=100.1950(10)°.
Volume: 600.674(18) Å$^3$
Z: 2
Density (calculated): 1.467 mg/m$^3$
Absorption coefficient: 2.592 mm$^{-1}$
F(000): 280
Crystal size: 0.44×0.20×0.12 mm$^3$
Reflections collected: 9112
Independent reflections: 2283 [R(int)=0.0214]
Refinement method: Full-matrix least-squares on $F^2$
Goodness-of-fit on $F^2$: 1.077
Final R indices [I>2sigma(I)] R1=0.0306, wR2=0.0808
R indices (all data): R1=0.0312, wR2=0.0812.

II. Single Crystal X-Ray Data for Compound 2 (FIG. 2):

A colorless plate crystal with dimensions 0.51×0.17×0.06 mm was mounted on a Nylon loop using very small amount of paratone oil.

Data were collected using a Bruker CCD (charge coupled device) based diffractometer equipped with an Oxford Cryostream low-temperature apparatus operating at 173 K. Data were measured using omega and phi scans of 0.5° per frame for 20 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software which corrects for Lp. Scaling and absorption corrections were applied using SADABS multi-scan technique, supplied by George Sheldrick. The structures are solved by the direct method using the SHELXS-97 program and refined by least squares method on $F^2$, SHELXL-97, which are incorporated in SHELXTL-PC V 6.10.

The structure was solved in the space group $P2_1/c$ (#14). All non-hydrogen atoms are refined anisotropically. Hydrogens were calculated by geometrical methods and refined as a riding model. The crystal used for the diffraction study showed no decomposition during data collection. All drawings are done at 50% ellipsoids.

Figure 2:
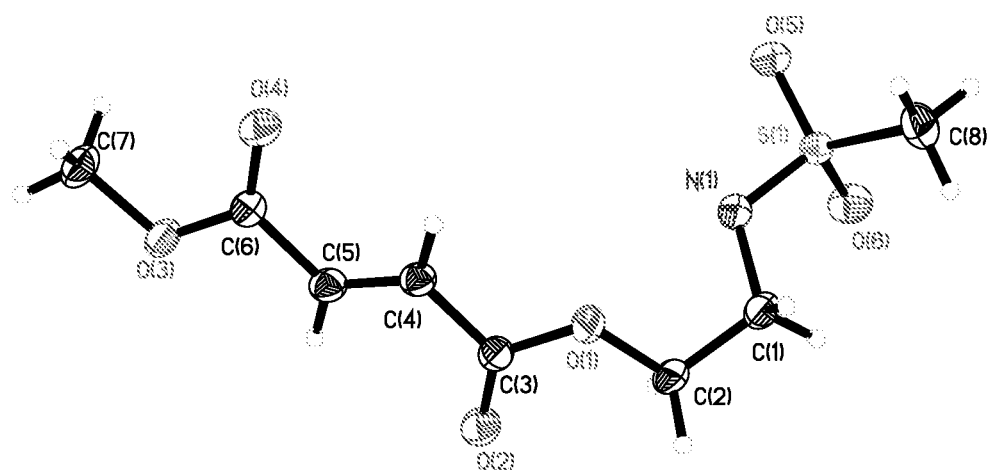
FIG. 2 depicts the single crystal X-ray structure of compound 2.

Compound 2 produced by the method described in Example 1 was analyzed. FIG. 2 depicts the unit cell. The single crystal x-ray data are included below:

Single Crystal Data:
Empirical formula: C8 H12 N O6 S
Formula weight: 250.25
Temperature: 173(2) K
Wavelength: 0.71073 Å
Space group: P $2_1$/c
Unit cell dimensions: a=11.9021(16) Å α=90°.
  b=5.4515(7) Å (β=95.554(2)°.
  c=17.404(2) Å γ=90°.
Volume: 1123.9(3) Å$^3$
Z: 4
Density (calculated): 1.479 mg/m$^3$
Absorption coefficient: 0.301 mm$^{-1}$
F(000): 524
Crystal size: 0.51×0.17×0.06 mm$^3$
Reflections collected: 8775
Independent reflections: 2063 [R(int)=0.0368]
Refinement method: Full-matrix least-squares on $F^2$
Goodness-of-fit on $F^2$: 1.053
Final R indices [I>2sigma(I)] R1=0.0356, wR2=0.0959
R indices (all data): R1=0.0419, wR2=0.1015

III. Single Crystal X-Ray Data for Compound 6 (FIG. 3):

A colorless plate crystal with dimensions 0.29×0.18×0.08 mm was mounted on a Nylon loop using very small amount of paratone oil.

Data were collected using a Bruker CCD (charge coupled device) based diffractometer equipped with an Oxford Cryostream low-temperature apparatus operating at 173 K. Data were measured using omega and phi scans of 0.5° per frame for 20 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software which corrects for Lp. Scaling and absorption corrections were applied using SADABS multi-scan technique, supplied by George Sheldrick. The structures are solved by the direct method using the SHELXS-97 program and refined by least squares method on $F^2$, SHELXL-97, which are incorporated in SHELXTL-PC V 6.10.

The structure was solved in the space group P-1 (#2). All non-hydrogen atoms are refined anisotropically. Hydrogens were calculated by geometrical methods and refined as a riding model. The crystal used for the diffraction study showed no decomposition during data collection. All drawings are done at 50% ellipsoids.

Figure 3:
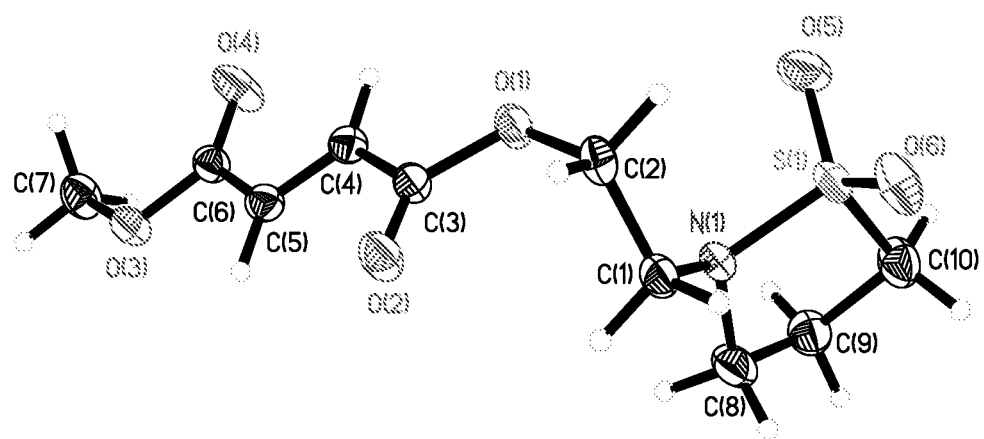
FIG. 3 depicts the single crystal X-ray structure of compound 6.

Compound 6 produced by the method described in Example 1 was analyzed. FIG. 3 depicts the unit cell. The single crystal x-ray data are included below:

Single Crystal Data:
Empirical formula: C10 H15 N O6 S
Formula weight: 277.29
Temperature: 173(2) K
Wavelength: 0.71073 Å
Space group: P-1

Unit cell dimensions: a=6.0125(10) Å α=102.435(2)°.
 b=9.1418(15) Å β=99.174(2)°.
 c=12.006(2) Å γ=105.445(2)°.
Volume: 604.45(17) Å$^3$
Z: 2
Density (calculated): 1.524 mg/m$^3$
Absorption coefficient: 0.288 mm$^{-1}$
F(000): 292
Crystal size: 0.29×0.19×0.08 mm$^3$
Reflections collected: 9989
Independent reflections: 2216 [R(int)=0.0389]
Refinement method: Full-matrix least-squares on F$^2$
Goodness-of-fit on F$^2$: 1.087
Final R indices [I>2sigma(I)] R1=0.0379, wR2=0.0983
R indices (all data): R1=0.0485, wR2=0.1062

Example 4

Delivery of MMF in Rats Upon Oral Administration of Prodrugs

Rats were obtained commercially and were pre-cannulated in the jugular vein. Animals were conscious at the time of the experiment. All animals were fasted overnight and until 4 hours post-dosing of a prodrug in the disclosure.

Blood samples (0.25 mL/sample) were collected from all animals at different time-points up to 24 hours post-dose into tubes containing sodium fluoride/sodium EDTA. Samples were centrifuged to obtain plasma. Plasma samples were transferred to plain tubes and stored at or below −70° C. prior to analysis.

To prepare analysis standards, 20 uL of rat plasma standard was quenched with 60 uL of internal standard. The sample tubes were vortexed for at least 1 min and then centrifuged at 3000 rpm for 10 min. 50 uL of supernatant was then transferred to 96-well plates containing 100 ul water for analysis by LC-MS-MS.

LC-MS/MS analysis was performed using an API 4000 equipped with HPLC and autosampler. The following HPLC column conditions were used: HPLC column: Waters Atlantis T3; flow rate 0.5 mL/min; run time 5 min; mobile phase A: 0.1% formic acid in water; mobile phase B: 0.1% formic acid in acetonitrile (ACN); gradient: 98% A/2% B at 0.0 min; 98% A/2% B at 1 min; 5% A/95% B at 3 min; 5% A/95% B at 3.75 min; 97% A/3% B at 4 min; and 98% A/2% B at 5.0 min. MMF was monitored in positive ion mode.

MMF, DMF or MMF prodrug was administered by oral gavage to groups of two to six adult male Sprague-Dawley rats (about 250 g). Animals were conscious at the time of the experiment. MMF, DMF or MMF prodrug was orally administered in an aqueous solution of 0.5% hydroxypropyl methyl cellulose (HPMC), 0.02% polysorbate 80, and 20 mM citrate buffer (pH 5), at a dose of 10 mg-equivalents MMF per kg body weight.

The percent absolute bioavailability (F %) of MMF was determined by comparing the area under the MMF concentration vs time curve (AUC) following oral administration of MMF, DMF or MMF prodrug with the AUC of the MMF concentration vs time curve following intravenous administration of MMF on a dose normalized basis.

The MMF prodrugs, when administered orally to rats at a dose of 10 mg/kg MMF-equivalents in the aqueous vehicle, exhibited an absolute oral bioavailability (relative to IV) ranging from about 3% to about 96% (See Table 3).

TABLE 3

| Compound | Percent Absolute Bioavailability (F %) |
| --- | --- |
| MMF | 69.6 |
| DMF | 69.6 |
| Compound 1 | 87.2-92.1 |

TABLE 3-continued

| Compound | Percent Absolute Bioavailability (F %) |
| --- | --- |
| Compound 2 | 66.1-95.3 |
| Compound 6 | 73.2-99.6 |

Example 5

Physical Stability of the Instant Prodrugs and DMF in Crystalline Form

Figure 4:
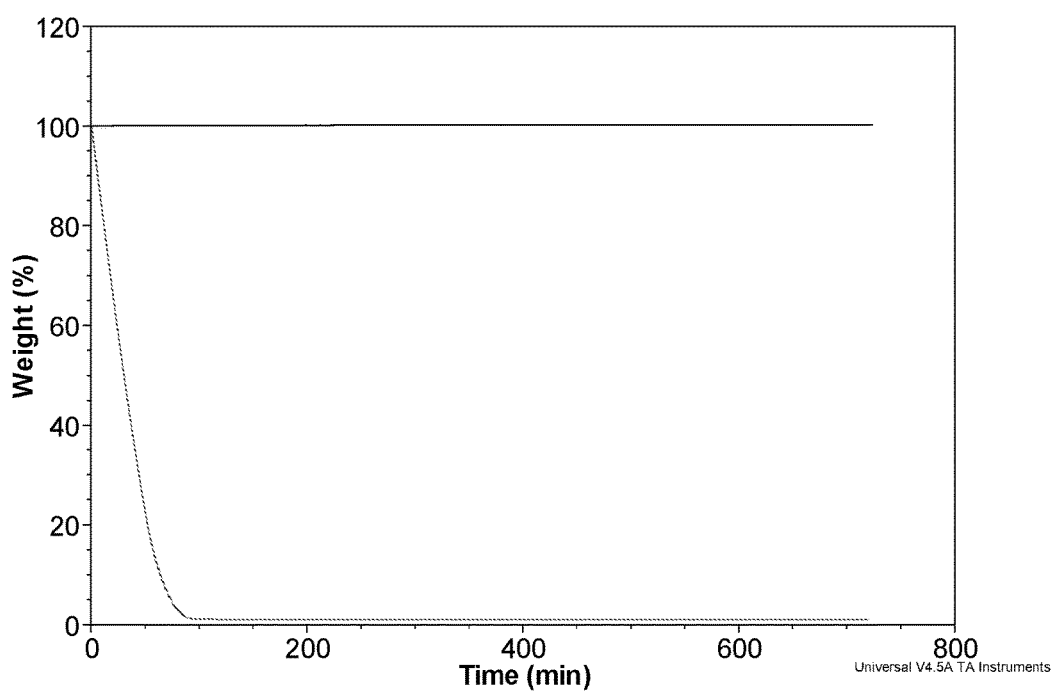
FIG. 4 depicts a TGA thermogram showing weight loss versus time for Compound 1 and DMF.
Figure 5:
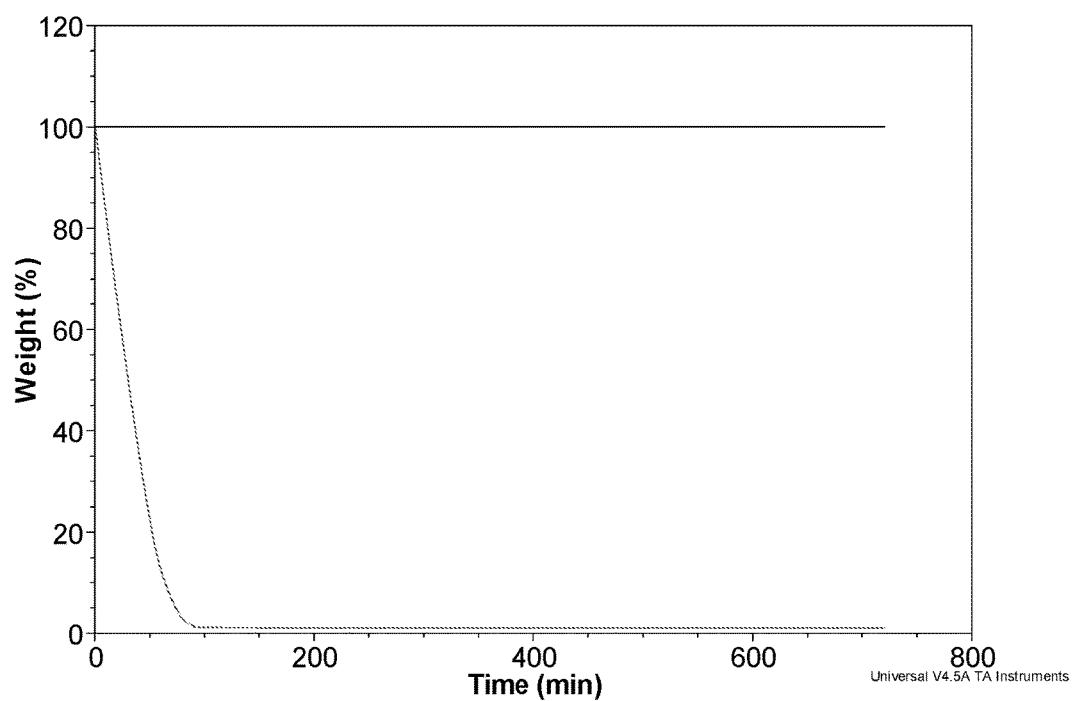
FIG. 5 depicts a TGA thermogram showing weight loss versus time for Compound 2 and DMF.

The physical stability of compounds of the present invention and dimethyl fumarate (DMF) were measured via thermogravimetric analysis (TGA). FIG. 4 shows a plot of weight loss at 55° C. vs time for Compound 1 (10.53 mg), no change, and DMF (4.97 mg), ~100% weight loss in less than 2 hours. FIG. 5 shows a plot of weight loss at 55° C. vs time for Compound 2 (9.20 mg), no change, and DMF (4.97 mg), ~100% weight loss in less than 2 hours. These data indicate that DMF undergoes sublimation while Compounds 1 and 2 are physically stable under similar conditions.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A pharmaceutical composition comprising:
   (i) a therapeutically effective amount of a compound of Formula (I), or a pharmaceutically acceptable salt thereof:

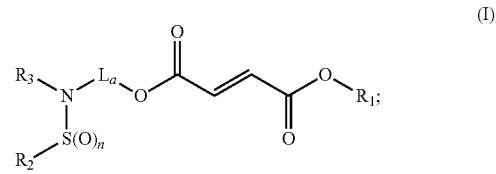

(I)

wherein:
R$_1$ is C$_1$-C$_6$ alkyl;
L$_a$ is C$_1$-C$_6$ alkyl, C$_3$-C$_{10}$ carbocycle, C$_6$-C$_{10}$ aryl, heterocycle comprising one or two 5- or 6-membered rings and 1-4 heteroatoms selected from N, O and S, or heteroaryl comprising one or two 5- or 6-membered rings and 1-4 heteroatoms selected from N, O and S, wherein the alkyl, carbocycle, aryl, heterocycle, or heteroaryl groups are optionally, independently substituted one or more times with halogen;
R$_2$ is C$_1$-C$_{10}$ alkyl, C$_2$-C$_6$ alkenyl, C$_2$-C$_6$ alkynyl, OH, C$_6$-C$_{10}$ aryl, C$_3$-C$_{10}$ carbocycle, heterocycle comprising one or two member 5- or 6-membered rings and 1-4 heteroatoms selected from N, O and S, or heteroaryl comprising one or two 5- or 6-membered rings and 1-4 heteroatoms selected from N, O and S, wherein the alkyl, alkenyl, alkynyl, aryl, carbocycle, heterocycle, or heteroaryl groups are optionally, independently substituted one or more times with C$_1$-C$_6$ alkyl, OH, O(C$_1$-C$_6$ alkyl), oxo, halogen, NH$_2$, N(H)(C$_1$-C$_6$ alkyl), N(C$_1$-C$_6$ alkyl)$_2$, SO$_2$H, SO$_2$(C$_1$-C$_6$ alkyl), CHO, CO$_2$H, CO$_2$(C$_1$-C$_6$ alkyl), or CN;

$R_3$ is H, $C_1$-$C_{10}$ alkyl, $C_2$-$C_6$ alkenyl, $C_2$-$C_6$ alkynyl, $SO_2R_4$, or $S(O)R_4$, wherein the alkyl, alkenyl, or alkynyl groups are optionally, independently substituted one or more times with $C_1$-$C_6$ alkyl, OH, $O(C_1$-$C_6$ alkyl), oxo, halogen, $NH_2$, $N(H)(C_1$-$C_6$ alkyl), $N(C_1$-$C_6$ alkyl)$_2$, $SO_2H$, $SO_2(C_1$-$C_6$ alkyl), CHO, $CO_2H$, $CO_2(C_1$-$C_6$ alkyl), or CN;

$R_4$ is $C_1$-$C_{10}$ alkyl, $C_2$-$C_6$ alkenyl, $C_2$-$C_6$ alkynyl, OH, $C_6$-$C_{10}$ aryl, $C_3$-$C_{10}$ carbocycle, heterocycle comprising one or two 5- or 6-member rings and 1-4 heteroatoms selected from N, O and S, or heteroaryl comprising one or two 5- or 6-member rings and 1-4 heteroatoms selected from N, O and S, wherein the alkyl, alkenyl, alkynyl, aryl, carbocycle, heterocycle, or heteroaryl groups are optionally, independently substituted one or more times with $C_1$-$C_6$ alkyl, OH, $O(C_1$-$C_6$ alkyl), oxo, halogen, $NH_2$, $N(H)(C_1$-$C_6$ alkyl), $N(C_1$-$C_6$ alkyl)$_2$, $SO_2H$, $SO_2(C_1$-$C_6$ alkyl), CHO, $CO_2H$, $CO_2(C_1$-$C_6$ alkyl), or CN;

or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and n is 1 or 2; and (ii) a pharmaceutically acceptable carrier or excipient.

2. A pharmaceutical composition comprising:
(i) a therapeutically effective amount of a compound of Formula (I), or a pharmaceutically acceptable salt thereof:

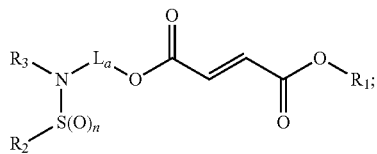

(I)

wherein:
$R_1$ is $C_1$-$C_6$ alkyl;
$L_a$ is a $C_1$-$C_6$ alkyl;
$R_2$ is $C_1$-$C_{10}$ alkyl optionally substituted by halo, or $C_6$-$C_{10}$ aryl optionally substituted by $C_1$-$C_{10}$ alkyl, OH, $O(C_1$-$C_6$ alkyl), or halo;
$R_3$ is H, $C_1$-$C_{10}$ alkyl, $SO_2R_4$, or $S(O)R_4$;
$R_4$ is $C_1$-$C_{10}$ alkyl optionally substituted by halo, or $C_6$-$C_{10}$ aryl optionally substituted by $C_1$-$C_{10}$ alkyl;
or alternatively, $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo; and
n is 1 or 2; and
(ii) a pharmaceutically acceptable carrier or excipient.

3. The pharmaceutical composition of claim 1, wherein $R_1$ is methyl.

4. The pharmaceutical composition of claim 2, wherein $R_1$ is methyl.

5. The pharmaceutical composition of claim 1, wherein $R_2$ is $C_1$-$C_{10}$ alkyl, or phenyl optionally substituted one or more times with $C_1$-$C_6$ alkyl, OH, or $O(C_1$-$C_6$ alkyl).

6. The pharmaceutical composition of claim 1, wherein $R_3$ is H or $C_1$-$C_{10}$ alkyl.

7. The pharmaceutical composition of claim 1, wherein $R_2$ and $R_3$, together with the atoms to which they are attached, form a cyclic moiety comprising one or two 5- or 6-membered rings, and optionally further comprising 1-5 additional heteroatoms selected from N, O and S, wherein the rings can be optionally substituted with oxo.

8. The pharmaceutical composition of claim 1, wherein $R_4$ is $C_1$-$C_{10}$ alkyl optionally substituted by halo, or $C_6$-$C_{10}$ aryl optionally substituted by $C_1$-$C_6$ alkyl.

9. The pharmaceutical composition of claim 1, wherein $L_a$ is a $C_1$-$C_6$ alkyl.

10. The pharmaceutical composition of claim 4, wherein $R_2$ is $C_1$-$C_{10}$ alkyl and $R_3$ is H or $C_1$-$C_{10}$ alkyl.

11. The pharmaceutical composition of claim 2, wherein the compound of Formula I is selected from the group consisting of:

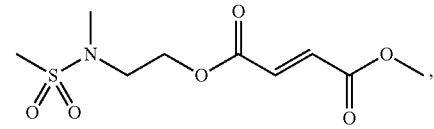

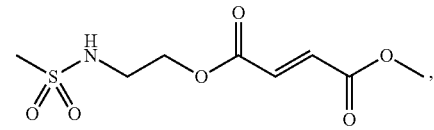

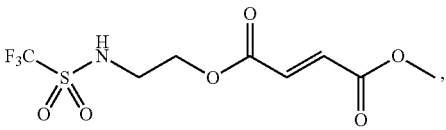

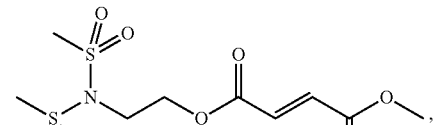

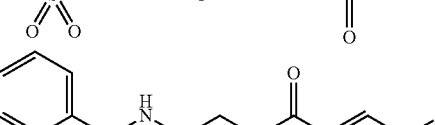

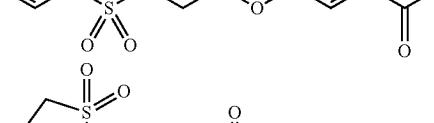

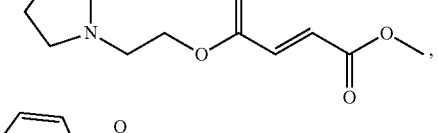

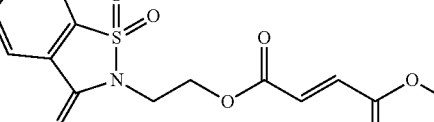

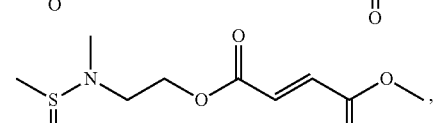

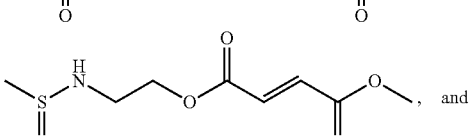, and

-continued

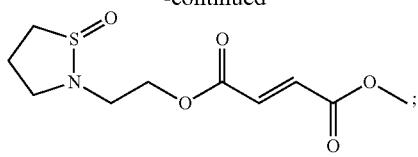

or a pharmaceutically acceptable salt thereof.

12. The pharmaceutical composition of claim 11, wherein the compound of Formula I is selected from the group consisting of:

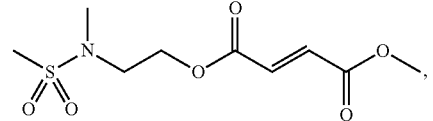

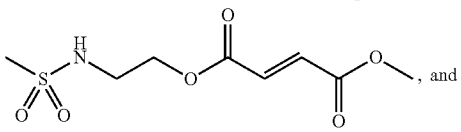

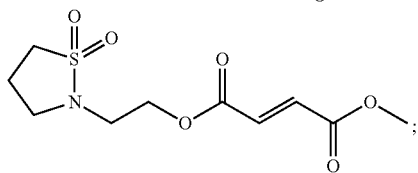

or a pharmaceutically acceptable salt thereof.

13. The pharmaceutical composition of claim 12, wherein the compound of Formula I is:

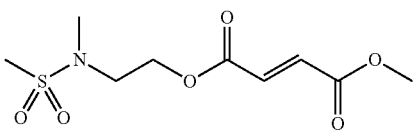

or a pharmaceutically acceptable salt thereof.

14. The pharmaceutical composition of claim 12, wherein the compound of Formula I is:

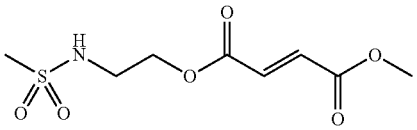

or a pharmaceutically acceptable salt thereof.

15. The pharmaceutical composition of claim 12, wherein the compound of Formula I is:

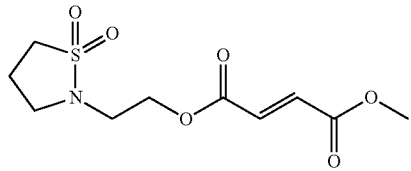 [SMILES: COC(=O)/C=C/C(=O)OCCN1CCCS1(=O)=O]

or a pharmaceutically acceptable salt thereof.

* * * * *